United States Patent
Pilletere et al.

(10) Patent No.: US 10,792,071 B2
(45) Date of Patent: Oct. 6, 2020

(54) SEALS FOR SURGICAL ACCESS ASSEMBLIES

(71) Applicant: Covidien LP, Mansfield, MA (US)

(72) Inventors: Roy J. Pilletere, North Haven, CT (US); Matthew A. Dinino, Newington, CT (US); Garrett P. Ebersole, Hamden, CT (US); Kevin Desjardin, Cheshire, CT (US); Justin Thomas, New Haven, CT (US); Jacob C. Baril, Norwalk, CT (US); Nicolette R. LaPierre, Windsor Locks, CT (US); Eric Brown, Haddam, CT (US)

(73) Assignee: Covidien LP, Mansfield, MA (US)

( * ) Notice: Subject to any disclaimer, the term of this patent is extended or adjusted under 35 U.S.C. 154(b) by 39 days.

(21) Appl. No.: 16/272,068

(22) Filed: Feb. 11, 2019

(65) Prior Publication Data

US 2020/0253634 A1 Aug. 13, 2020

(51) Int. Cl.
*A61B 17/34* (2006.01)

(52) U.S. Cl.
CPC ...... *A61B 17/3498* (2013.01); *A61B 17/3423* (2013.01)

(58) Field of Classification Search
CPC . A61B 17/34; A61B 17/3421; A61B 17/3423; A61B 17/3462; A61B 17/3498; A61B 2017/3425; A61B 2017/3427; A61B 2017/3439; A61B 2017/3441; A61B 2017/3443; A61B 2017/3445; A61B 2017/345; A61B 2017/3464
See application file for complete search history.

(56) References Cited

U.S. PATENT DOCUMENTS

| 3,402,710 A | 9/1968 | Paleschuck |
| 3,495,586 A | 2/1970 | Regenbogen |
(Continued)

FOREIGN PATENT DOCUMENTS

| CA | 2702419 A1 | 11/2010 |
| EP | 0226026 A2 | 6/1987 |
(Continued)

OTHER PUBLICATIONS

U.S. Appl. No. 16/394,043, filed Apr. 25, 2019, inventor Lorenzo Vaccarella.

(Continued)

*Primary Examiner* — Eric S Gibson
(74) *Attorney, Agent, or Firm* — Carter, DeLuca & Farrell LLP

(57) ABSTRACT

Access assemblies includes an instrument valve housing and a valve assembly disposed within the cavity of the instrument valve housing. The valve assembly includes a guard assembly, a seal assembly disposed adjacent to the guard assembly, and a centering mechanism for maintaining the seal assembly and guard assembly centered within a cavity of the instrument valve. In embodiments, the seal assembly includes a plurality of seal sections that are movable from an unfolded configuration to folded configuration in which the seal assembly forms a hexagonal member defining an opening to facilitate sealed passage of a surgical instrument. The seal sections may include a tapered inner edge for engaging a surgical instrument inserted through the instrument valve housing.

15 Claims, 10 Drawing Sheets

(56) References Cited

U.S. PATENT DOCUMENTS

| | | | |
|---|---|---|---|
| 4,016,884 A | 4/1977 | Kwan-Gett | |
| 4,112,932 A | 9/1978 | Chiulli | |
| 4,183,357 A | 1/1980 | Bentley et al. | |
| 4,356,826 A | 11/1982 | Kubota | |
| 4,402,683 A | 9/1983 | Kopman | |
| 4,653,476 A | 3/1987 | Bonnet | |
| 4,737,148 A | 4/1988 | Blake | |
| 4,863,430 A | 9/1989 | Klyce et al. | |
| 4,863,438 A | 9/1989 | Gauderer et al. | |
| 4,984,564 A | 1/1991 | Yuen | |
| 5,002,557 A | 3/1991 | Hasson | |
| 5,073,169 A | 12/1991 | Raiken | |
| 5,082,005 A | 1/1992 | Kaldany | |
| 5,122,122 A | 6/1992 | Allgood | |
| 5,159,921 A | 11/1992 | Hoover | |
| 5,176,697 A | 1/1993 | Hasson et al. | |
| 5,183,471 A | 2/1993 | Wilk | |
| 5,192,301 A | 3/1993 | Kamiya et al. | |
| 5,209,741 A | 5/1993 | Spaeth | |
| 5,209,754 A | 5/1993 | Ahluwalia | |
| 5,217,466 A | 6/1993 | Hasson | |
| 5,242,409 A | 9/1993 | Buelna | |
| 5,242,415 A | 9/1993 | Kantrowitz et al. | |
| 5,257,973 A | 11/1993 | Villasuso | |
| 5,257,975 A | 11/1993 | Foshee | |
| 5,269,772 A | 12/1993 | Wilk | |
| 5,290,249 A | 3/1994 | Foster et al. | |
| 5,312,391 A | 5/1994 | Wilk | |
| 5,312,417 A | 5/1994 | Wilk | |
| 5,314,417 A | 5/1994 | Stephens et al. | |
| 5,318,516 A | 6/1994 | Cosmescu | |
| 5,330,486 A | 7/1994 | Wilk | |
| 5,334,143 A | 8/1994 | Carroll | |
| 5,336,169 A | 8/1994 | Divilio et al. | |
| 5,336,203 A | 8/1994 | Goldhardt et al. | |
| 5,337,937 A | 8/1994 | Remiszewski et al. | |
| 5,345,927 A | 9/1994 | Bonutti | |
| 5,360,417 A | 11/1994 | Gravener et al. | |
| 5,366,478 A | 11/1994 | Brinkerhoff et al. | |
| 5,375,588 A | 12/1994 | Yoon | |
| 5,378,588 A | 1/1995 | Tsuchiya | |
| 5,391,156 A | 2/1995 | Hildwein et al. | |
| 5,394,863 A | 3/1995 | Sanford et al. | |
| 5,395,367 A | 3/1995 | Wilk | |
| 5,437,683 A | 8/1995 | Neumann et al. | |
| 5,445,615 A | 8/1995 | Yoon | |
| 5,451,222 A | 9/1995 | De Maagd et al. | |
| 5,460,170 A | 10/1995 | Hammerslag | |
| 5,464,409 A | 11/1995 | Mohajer | |
| 5,480,410 A | 1/1996 | Cuschieri et al. | |
| 5,490,843 A | 2/1996 | Hildwein et al. | |
| 5,496,280 A * | 3/1996 | Vandenbroek | A61B 17/3498 |
| | | | 604/167.03 |
| 5,507,758 A | 4/1996 | Thomason et al. | |
| 5,511,564 A | 4/1996 | Wilk | |
| 5,514,133 A | 5/1996 | Golub et al. | |
| 5,514,153 A | 5/1996 | Bonutti | |
| 5,520,698 A | 5/1996 | Koh | |
| 5,522,791 A | 6/1996 | Leyva | |
| 5,524,644 A | 6/1996 | Crook | |
| 5,540,648 A | 7/1996 | Yoon | |
| 5,545,150 A | 8/1996 | Danks et al. | |
| 5,545,179 A | 8/1996 | Williamson, IV | |
| 5,556,385 A | 9/1996 | Andersen | |
| 5,569,159 A | 10/1996 | Anderson et al. | |
| 5,577,993 A | 11/1996 | Zhu et al. | |
| 5,601,581 A | 2/1997 | Fogarty et al. | |
| 5,603,702 A * | 2/1997 | Smith | A61B 17/3462 |
| | | | 251/149.1 |
| 5,624,399 A | 4/1997 | Ackerman | |
| 5,628,732 A * | 5/1997 | Antoon, Jr. | A61B 17/3462 |
| | | | 604/167.06 |
| 5,634,911 A | 6/1997 | Hermann et al. | |
| 5,634,937 A | 6/1997 | Mollenauer et al. | |
| 5,643,285 A | 7/1997 | Rowden et al. | |
| 5,649,550 A | 7/1997 | Crook | |
| 5,651,771 A | 7/1997 | Tangherlini et al. | |
| 5,653,705 A | 8/1997 | de la Torre et al. | |
| 5,656,013 A | 8/1997 | Yoon | |
| 5,672,168 A | 9/1997 | de la Torre et al. | |
| 5,683,378 A | 11/1997 | Christy | |
| 5,685,857 A | 11/1997 | Negus et al. | |
| 5,697,946 A | 12/1997 | Hopper et al. | |
| 5,709,675 A | 1/1998 | Williams | |
| 5,713,858 A | 2/1998 | Heruth et al. | |
| 5,713,869 A | 2/1998 | Morejon | |
| 5,722,962 A | 3/1998 | Garcia | |
| 5,728,103 A | 3/1998 | Picha et al. | |
| 5,730,748 A | 3/1998 | Fogarty et al. | |
| 5,735,791 A | 4/1998 | Alexander, Jr. et al. | |
| 5,741,298 A | 4/1998 | MacLeod | |
| 5,752,970 A | 5/1998 | Yoon | |
| 5,782,817 A | 7/1998 | Franzel et al. | |
| 5,795,290 A | 8/1998 | Bridges | |
| 5,803,921 A | 9/1998 | Bonadio | |
| 5,810,712 A | 9/1998 | Dunn | |
| 5,813,409 A | 9/1998 | Leahy et al. | |
| 5,830,191 A | 11/1998 | Hildwein et al. | |
| 5,836,871 A | 11/1998 | Wallace et al. | |
| 5,836,913 A | 11/1998 | Orth et al. | |
| 5,840,077 A | 11/1998 | Rowden et al. | |
| 5,842,971 A | 12/1998 | Yoon | |
| 5,848,992 A | 12/1998 | Hart et al. | |
| 5,853,417 A | 12/1998 | Fogarty et al. | |
| 5,857,461 A | 1/1999 | Levitsky et al. | |
| 5,865,817 A | 2/1999 | Moenning et al. | |
| 5,871,474 A | 2/1999 | Hermann et al. | |
| 5,876,413 A | 3/1999 | Fogarty et al. | |
| 5,894,843 A | 4/1999 | Benetti et al. | |
| 5,899,208 A | 5/1999 | Bonadio | |
| 5,899,913 A | 5/1999 | Fogarty et al. | |
| 5,904,703 A | 5/1999 | Gilson | |
| 5,906,577 A | 5/1999 | Beane et al. | |
| 5,914,415 A | 6/1999 | Tago | |
| 5,916,198 A | 6/1999 | Dillow | |
| 5,941,898 A | 8/1999 | Moenning et al. | |
| 5,951,588 A | 9/1999 | Moenning | |
| 5,957,913 A | 9/1999 | de la Torre et al. | |
| 5,964,781 A | 10/1999 | Mollenauer et al. | |
| 5,976,174 A | 11/1999 | Ruiz | |
| 5,989,224 A * | 11/1999 | Exline | A61B 17/3462 |
| | | | 604/167.02 |
| 5,997,515 A | 12/1999 | de la Torre et al. | |
| 6,017,355 A | 1/2000 | Hessel et al. | |
| 6,018,094 A | 1/2000 | Fox | |
| 6,024,736 A | 2/2000 | de la Torre et al. | |
| 6,030,402 A | 2/2000 | Thompson et al. | |
| 6,033,426 A | 3/2000 | Kaji | |
| 6,033,428 A | 3/2000 | Sardella | |
| 6,042,573 A | 3/2000 | Lucey | |
| 6,048,309 A | 4/2000 | Flom et al. | |
| 6,059,816 A | 5/2000 | Moenning | |
| 6,068,639 A | 5/2000 | Fogarty et al. | |
| 6,077,288 A | 6/2000 | Shimomura et al. | |
| 6,086,603 A | 7/2000 | Termin et al. | |
| 6,099,506 A | 8/2000 | Macoviak et al. | |
| 6,110,154 A | 8/2000 | Shimomura et al. | |
| 6,142,936 A | 11/2000 | Beane et al. | |
| 6,156,006 A | 12/2000 | Brosens et al. | |
| 6,162,196 A | 12/2000 | Hart et al. | |
| 6,171,282 B1 | 1/2001 | Ragsdale | |
| 6,197,002 B1 | 3/2001 | Peterson | |
| 6,217,555 B1 | 4/2001 | Hart et al. | |
| 6,228,063 B1 | 5/2001 | Aboul-Hosn | |
| 6,234,958 B1 | 5/2001 | Snoke et al. | |
| 6,238,373 B1 | 5/2001 | de la Torre et al. | |
| 6,241,768 B1 | 6/2001 | Agarwal et al. | |
| 6,251,119 B1 | 6/2001 | Addis | |
| 6,254,534 B1 | 7/2001 | Butler et al. | |
| 6,264,604 B1 | 7/2001 | Kieturakis et al. | |
| 6,276,661 B1 | 8/2001 | Laird | |
| 6,293,952 B1 | 9/2001 | Brosens et al. | |
| 6,315,770 B1 | 11/2001 | de la Torre et al. | |
| 6,319,246 B1 | 11/2001 | de la Torre et al. | |

(56) References Cited

U.S. PATENT DOCUMENTS

| | | |
|---|---|---|
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,702,787 B2 * | 3/2004 | Racenet ............ A61B 17/34 604/158 |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,981,966 B2 * | 1/2006 | Green ............ A61M 39/06 604/167.02 |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,012,128 B2 * | 9/2011 | Franer ............ A61B 17/3462 604/164.07 |
| 8,021,296 B2 | 9/2011 | Bonadio et al. |
| 8,025,670 B2 | 9/2011 | Sharp et al. |
| 8,029,475 B2 * | 10/2011 | Franer ............ A61B 17/3498 604/167.01 |

(56) References Cited

U.S. PATENT DOCUMENTS

| | | | |
|---|---|---|---|
| 8,038,652 B2 | 10/2011 | Morrison et al. | |
| 8,066,673 B2 | 11/2011 | Hart et al. | |
| 8,079,986 B2 | 12/2011 | Taylor et al. | |
| 8,092,430 B2 | 1/2012 | Richard et al. | |
| 8,105,234 B2 | 1/2012 | Ewers et al. | |
| 8,109,873 B2 | 2/2012 | Albrecht et al. | |
| 8,157,786 B2 | 4/2012 | Miller et al. | |
| 8,157,817 B2 | 4/2012 | Bonadio et al. | |
| 8,187,177 B2 | 5/2012 | Kahle et al. | |
| 8,187,178 B2 | 5/2012 | Bonadio et al. | |
| 8,241,209 B2 | 8/2012 | Shelton, IV et al. | |
| 8,262,568 B2 | 9/2012 | Albrecht et al. | |
| 8,323,184 B2 | 12/2012 | Spiegal et al. | |
| 8,335,783 B2 | 12/2012 | Milby | |
| 8,343,047 B2 | 1/2013 | Albrecht et al. | |
| 8,353,824 B2 | 1/2013 | Shelton, IV et al. | |
| 8,403,889 B2 | 3/2013 | Richard | |
| 8,409,084 B2 * | 4/2013 | Battles | A61B 17/3462 600/204 |
| 8,480,683 B2 | 7/2013 | Fowler et al. | |
| 8,574,153 B2 | 11/2013 | Richard | |
| 8,585,632 B2 | 11/2013 | Okoniewski | |
| 2001/0037053 A1 | 11/2001 | Bonadio et al. | |
| 2002/0055714 A1 | 5/2002 | Rothschild | |
| 2002/0072713 A1 * | 6/2002 | Almond | A61B 17/3462 604/167.05 |
| 2003/0014076 A1 | 1/2003 | Mollenauer et al. | |
| 2003/0093104 A1 | 5/2003 | Bonner et al. | |
| 2003/0187376 A1 | 10/2003 | Rambo | |
| 2003/0233115 A1 | 12/2003 | Eversull et al. | |
| 2003/0236549 A1 | 12/2003 | Bonadio et al. | |
| 2004/0059297 A1 | 3/2004 | Racenet et al. | |
| 2004/0092795 A1 | 5/2004 | Bonadio et al. | |
| 2004/0102804 A1 | 5/2004 | Chin | |
| 2004/0111061 A1 | 6/2004 | Curran | |
| 2004/0138529 A1 | 7/2004 | Wiltshire et al. | |
| 2004/0204734 A1 | 10/2004 | Wagner et al. | |
| 2004/0267096 A1 | 12/2004 | Caldwell et al. | |
| 2005/0020884 A1 | 1/2005 | Hart et al. | |
| 2005/0070850 A1 * | 3/2005 | Albrecht | A61B 17/34 604/167.03 |
| 2005/0070851 A1 * | 3/2005 | Thompson | A61B 17/3462 604/167.03 |
| 2005/0070935 A1 | 3/2005 | Ortiz | |
| 2005/0070943 A1 * | 3/2005 | Hueil | A61B 17/3462 606/167 |
| 2005/0070946 A1 * | 3/2005 | Franer | A61B 17/3498 606/185 |
| 2005/0070947 A1 * | 3/2005 | Franer | A61B 17/3462 606/185 |
| 2005/0077688 A1 * | 4/2005 | Voegele | A61B 17/3462 277/628 |
| 2005/0077689 A1 * | 4/2005 | Hueil | A61B 17/3421 277/628 |
| 2005/0096695 A1 | 5/2005 | Olich | |
| 2005/0119525 A1 | 6/2005 | Takemoto | |
| 2005/0137459 A1 | 6/2005 | Chin et al. | |
| 2005/0148823 A1 | 7/2005 | Vaugh et al. | |
| 2005/0192483 A1 | 9/2005 | Bonadio et al. | |
| 2005/0203346 A1 | 9/2005 | Bonadio et al. | |
| 2005/0209608 A1 | 9/2005 | O'Heeron | |
| 2005/0245876 A1 | 11/2005 | Khosravi et al. | |
| 2005/0251092 A1 | 11/2005 | Howell et al. | |
| 2005/0277946 A1 | 12/2005 | Greenhalgh | |
| 2006/0071432 A1 | 4/2006 | Staudner | |
| 2006/0129165 A1 | 6/2006 | Edoga et al. | |
| 2006/0149137 A1 | 7/2006 | Pingleton et al. | |
| 2006/0149306 A1 | 7/2006 | Hart et al. | |
| 2006/0161049 A1 | 7/2006 | Beane et al. | |
| 2006/0161050 A1 | 7/2006 | Butler et al. | |
| 2006/0212063 A1 | 9/2006 | Wilk | |
| 2006/0224161 A1 | 10/2006 | Bhattacharyya | |
| 2006/0241651 A1 | 10/2006 | Wilk | |
| 2006/0247498 A1 | 11/2006 | Bonadio et al. | |
| 2006/0247499 A1 | 11/2006 | Butler et al. | |
| 2006/0247500 A1 | 11/2006 | Voegele et al. | |
| 2006/0247516 A1 | 11/2006 | Hess et al. | |
| 2006/0247586 A1 | 11/2006 | Voegele et al. | |
| 2006/0247673 A1 | 11/2006 | Voegele et al. | |
| 2006/0247678 A1 | 11/2006 | Weisenburgh et al. | |
| 2006/0264992 A1 * | 11/2006 | Franer | A61B 17/3462 606/167 |
| 2006/0270911 A1 | 11/2006 | Voegele et al. | |
| 2007/0093695 A1 | 4/2007 | Bonadio et al. | |
| 2007/0118175 A1 | 5/2007 | Butler et al. | |
| 2007/0151566 A1 | 7/2007 | Kahle et al. | |
| 2007/0203398 A1 | 8/2007 | Bonadio et al. | |
| 2007/0208312 A1 | 9/2007 | Norton et al. | |
| 2007/0225650 A1 | 9/2007 | Hart et al. | |
| 2007/0270654 A1 | 11/2007 | Pignato et al. | |
| 2007/0270882 A1 | 11/2007 | Hjelle et al. | |
| 2008/0009826 A1 | 1/2008 | Miller et al. | |
| 2008/0021360 A1 | 1/2008 | Fihe et al. | |
| 2008/0027476 A1 | 1/2008 | Piskun | |
| 2008/0048011 A1 | 2/2008 | Weller | |
| 2008/0091143 A1 | 4/2008 | Taylor et al. | |
| 2008/0097162 A1 | 4/2008 | Bonadio et al. | |
| 2008/0097332 A1 | 4/2008 | Greenhalgh et al. | |
| 2008/0119868 A1 | 5/2008 | Sharp et al. | |
| 2008/0161826 A1 | 7/2008 | Guiraudon | |
| 2008/0188868 A1 | 8/2008 | Weitzner et al. | |
| 2008/0194973 A1 | 8/2008 | Imam | |
| 2008/0200767 A1 | 8/2008 | Ewers et al. | |
| 2008/0255519 A1 | 10/2008 | Piskun et al. | |
| 2008/0319261 A1 | 12/2008 | Lucini et al. | |
| 2009/0012477 A1 | 1/2009 | Norton et al. | |
| 2009/0036738 A1 | 2/2009 | Cuschieri et al. | |
| 2009/0036745 A1 | 2/2009 | Bonadio et al. | |
| 2009/0093752 A1 | 4/2009 | Richard et al. | |
| 2009/0093850 A1 | 4/2009 | Richard | |
| 2009/0105635 A1 | 4/2009 | Bettuchi et al. | |
| 2009/0131751 A1 | 5/2009 | Spivey et al. | |
| 2009/0137879 A1 | 5/2009 | Ewers et al. | |
| 2009/0182279 A1 | 7/2009 | Wenchell et al. | |
| 2009/0182288 A1 | 7/2009 | Spenciner | |
| 2009/0187079 A1 | 7/2009 | Albrecht et al. | |
| 2009/0204067 A1 | 8/2009 | Abu-Halawa | |
| 2009/0221968 A1 | 9/2009 | Morrison et al. | |
| 2009/0227843 A1 | 9/2009 | Smith et al. | |
| 2009/0326330 A1 | 12/2009 | Bonadio et al. | |
| 2009/0326332 A1 | 12/2009 | Carter | |
| 2010/0063452 A1 | 3/2010 | Edelman et al. | |
| 2010/0100043 A1 | 4/2010 | Racenet | |
| 2010/0113886 A1 | 5/2010 | Piskun et al. | |
| 2010/0160938 A9 * | 6/2010 | Franer | A61B 17/3462 606/167 |
| 2010/0228094 A1 | 9/2010 | Ortiz et al. | |
| 2010/0240960 A1 | 9/2010 | Richard | |
| 2010/0249516 A1 | 9/2010 | Shelton, IV et al. | |
| 2010/0249523 A1 | 9/2010 | Spiegal et al. | |
| 2010/0249524 A1 | 9/2010 | Ransden et al. | |
| 2010/0262080 A1 | 10/2010 | Shelton, IV et al. | |
| 2010/0280326 A1 | 11/2010 | Hess et al. | |
| 2010/0286484 A1 | 11/2010 | Stellon et al. | |
| 2010/0286506 A1 | 11/2010 | Ransden et al. | |
| 2010/0298646 A1 | 11/2010 | Stellon et al. | |
| 2010/0312063 A1 | 12/2010 | Hess et al. | |
| 2010/0312065 A1 * | 12/2010 | Shelton, IV | A61B 90/98 600/207 |
| 2011/0009704 A1 | 1/2011 | Marczyk et al. | |
| 2011/0021877 A1 | 1/2011 | Fortier et al. | |
| 2011/0028891 A1 | 2/2011 | Okoniewski | |
| 2011/0034778 A1 | 2/2011 | Kleyman | |
| 2011/0054257 A1 | 3/2011 | Stopek | |
| 2011/0054258 A1 | 3/2011 | O'Keefe et al. | |
| 2011/0054260 A1 | 3/2011 | Albrecht et al. | |
| 2011/0082341 A1 | 4/2011 | Kleyman et al. | |
| 2011/0082343 A1 | 4/2011 | Okoniewski | |
| 2011/0082346 A1 | 4/2011 | Stopek | |
| 2011/0118553 A1 | 5/2011 | Stopek | |
| 2011/0124968 A1 | 5/2011 | Kleyman | |
| 2011/0124969 A1 | 5/2011 | Stopek | |
| 2011/0124970 A1 | 5/2011 | Kleyman | |

(56) References Cited

U.S. PATENT DOCUMENTS

| | | |
|---|---|---|
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251560 A1* | 10/2011 | Albrecht ............ A61B 17/3462 604/167.01 |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0223833 A1* | 8/2015 | Coffeen ............ A61B 17/3462 600/204 |
| 2020/0113598 A1* | 4/2020 | Evans ................ A61B 17/3423 |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 1994896 A1 | 11/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2014116889 A1 | 7/2014 |
| WO | 2016110720 A1 | 7/2016 |
| WO | 2016186905 A1 | 11/2016 |

OTHER PUBLICATIONS

U.S. Appl. No. 16/238,823, filed Jan. 3, 2019, inventor Garrett Ebersole.

European Search Report dated Jul. 3, 2020, issued in EP Appln. No. 20156174, 8 pages.

* cited by examiner

SEALS FOR SURGICAL ACCESS ASSEMBLIES

BACKGROUND

Technical Field

The present disclosure relates to access assemblies for minimally invasive surgery, including seals. More particularly, the present disclosure relates to seals for surgical access assemblies.

Background

In order to facilitate minimally invasive surgery, a working space must be created in the desired surgical space. An insufflation gas, typically $CO_2$, is introduced into the abdomen of the patient to create an inflated state called a pneumoperitoneum. Access assemblies are utilized to allow the introduction of surgical instrumentation and endoscopes (or other visualization tools). These access assemblies maintain the pressure for the pneumoperitoneum, as they have one or more seals that adapt to the surgical instrumentation. Typically, a "zero-seal" in the access assembly seals the access assembly in the absence of a surgical instrument in the access assembly, and an instrument seal seals around a surgical instrument that has been inserted through the access assembly.

The breadth of surgical instrumentation on the market today requires a robust seal capable adjusting to multiple sizes and withstanding multiple insertions of surgical instrumentation. Some of the instrumentation can include sharp edges that can tear or otherwise damage seals. Therefore, it would be beneficial to have an access assembly with improved seal durability.

SUMMARY

An access assembly with an improved seal durability is provided. The access assembly includes an instrument valve housing and a valve assembly. The instrument valve housing includes upper, lower, and inner housing sections and defines a cavity. The valve assembly is disposed within the cavity of the instrument valve housing. The valve assembly includes a guard assembly, a seal assembly disposed adjacent to the guard assembly, and a centering mechanism for maintaining the seal assembly and guard assembly centered within the cavity of the instrument valve. The guard assembly includes a plurality of guard sections. The seal assembly is disposed adjacent to the guard assembly, the seal assembly including a plurality of seal sections, the plurality of seal sections being movable from an unfolded configuration to folded configuration in which the seal assembly forms a hexagonal member defining an opening to facilitate sealed passage of a surgical instrument.

In embodiments, an opening in the seal assembly has a diameter between 0.025" and 0.100". The seal assembly may include six seal sections. The plurality of seal sections may be formed of polyisoprenes or silicone elastomers. Seal sections of the plurality of seal sections may be connected to adjacent seal sections of the plurality of seal sections by connector portions. The connector portions may include living hinges. Each seal section of the plurality of seal sections may include a wing shape.

In some embodiments, an inner edge of each seal section of the plurality of seal sections is straight. Alternatively, the inner edge of each seal section of the plurality of seal sections defines a V-shape. The V-shape may include an angle between one hundred eighty degrees and two hundred seventy-five degrees. The inner edge of each seal section of the plurality of seal sections may be tapered. The plurality of seal sections may include first, second, third, fourth, fifth, and sixth seal sections. Each of the first, second, third, fourth, fifth, and sixth seal sections may overlap the adjacent second, third, fourth, fifth, sixth, and first seal sections.

The access assembly may further include a retainer assembly including upper and lower retainer members. At least one of the upper and lower retainer members may include a plurality of pins receivable through the guard assembly and seal assembly for retaining the guard and seal assemblies relative to each other. The centering mechanism may include a bellows.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
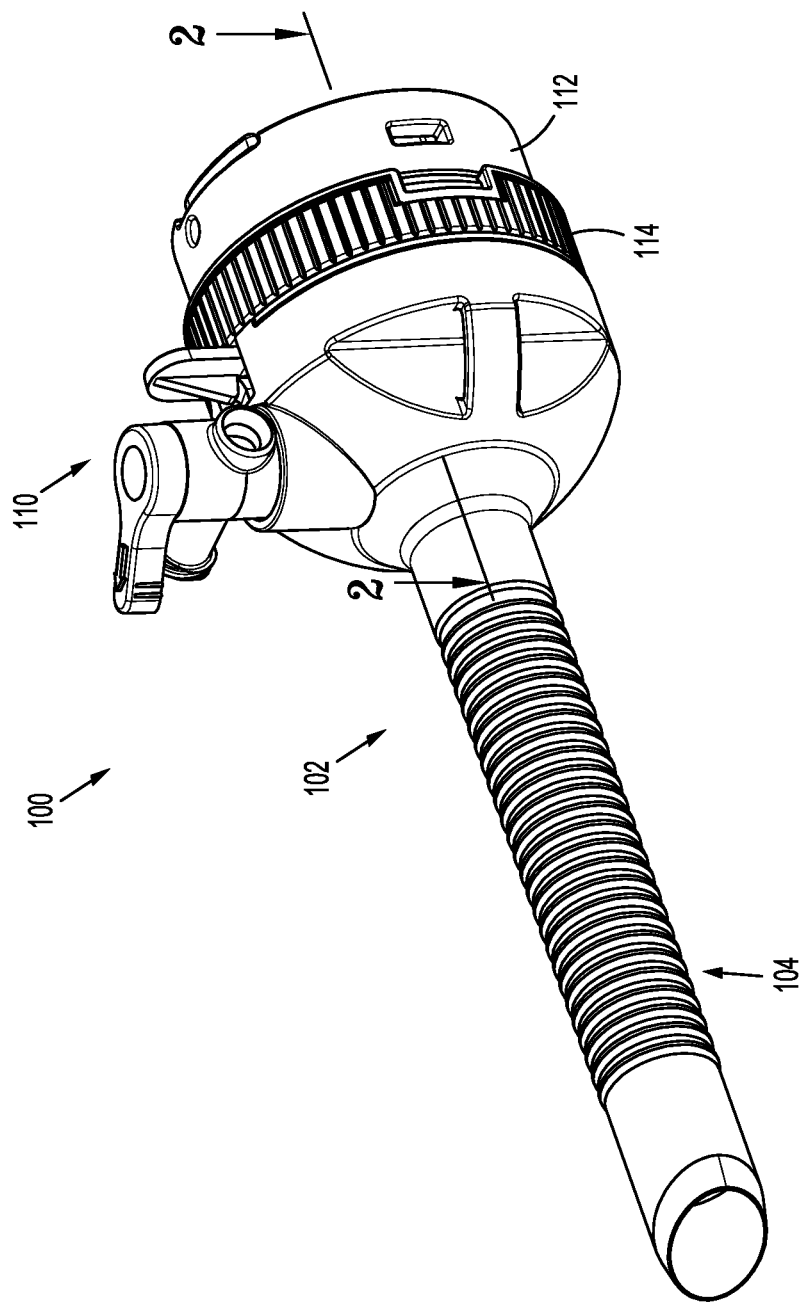
FIG. 1 is a side perspective view of an access assembly according to an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Access assemblies with obturators are employed during minimally invasive surgery, e.g., laparoscopic surgery, and provide for the sealed access of surgical instruments into an insufflated body cavity, such as the abdominal cavity. The access assemblies of the present disclosure include an instrument valve housing mounted on a cannula tube, and include an obturator (not shown) inserted through the valve housing and cannula. The obturator can have a blunt distal end, or a bladed or non-bladed penetrating distal end and can be used to incise the abdominal wall so that the access assembly can be introduced into the abdomen. The handle of the obturator can engage or selectively lock into the instrument valve housing of the access assembly.

Access assemblies are employed to tunnel through an anatomical structure, e.g., the abdominal wall, either by making a new passage through the anatomical structure or by passing through an existing opening through the anatomical structure. Once the trocar assembly with the obturator has tunneled through the anatomical structure, the obturator is removed, leaving the access assembly in place. The instrument valve housing of the access assembly includes valves that prevent the escape of insufflation gases from the body cavity, while also allowing surgical instruments to be inserted into the cavity.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of an obturator. The bladeless obturator may be provided for the blunt dissection of the abdominal lining during a surgical procedure.

Various trocar obturators suitable for use with the access assembly of the present disclosure are known and include, for example, bladed, bladeless, blunt, optical, and non-optical. For a detailed description of the structure and function of exemplary trocar assemblies, including exemplar trocar obturators and exemplar cannulas, please refer to commonly owned PCT Publication No. WO 2016/186905 ("the '905 publication"), the content of which is hereby incorporated by reference herein in its entirety.

With initial reference now to FIG. 1, an access assembly according to aspects of the present disclosure is shown generally as access assembly 100. The access assembly 100 includes a cannula 102 and an instrument valve housing 110 secured to the cannula 102. For a detailed description of an exemplary access assembly, please refer to the '905 publication.

Figure 2:
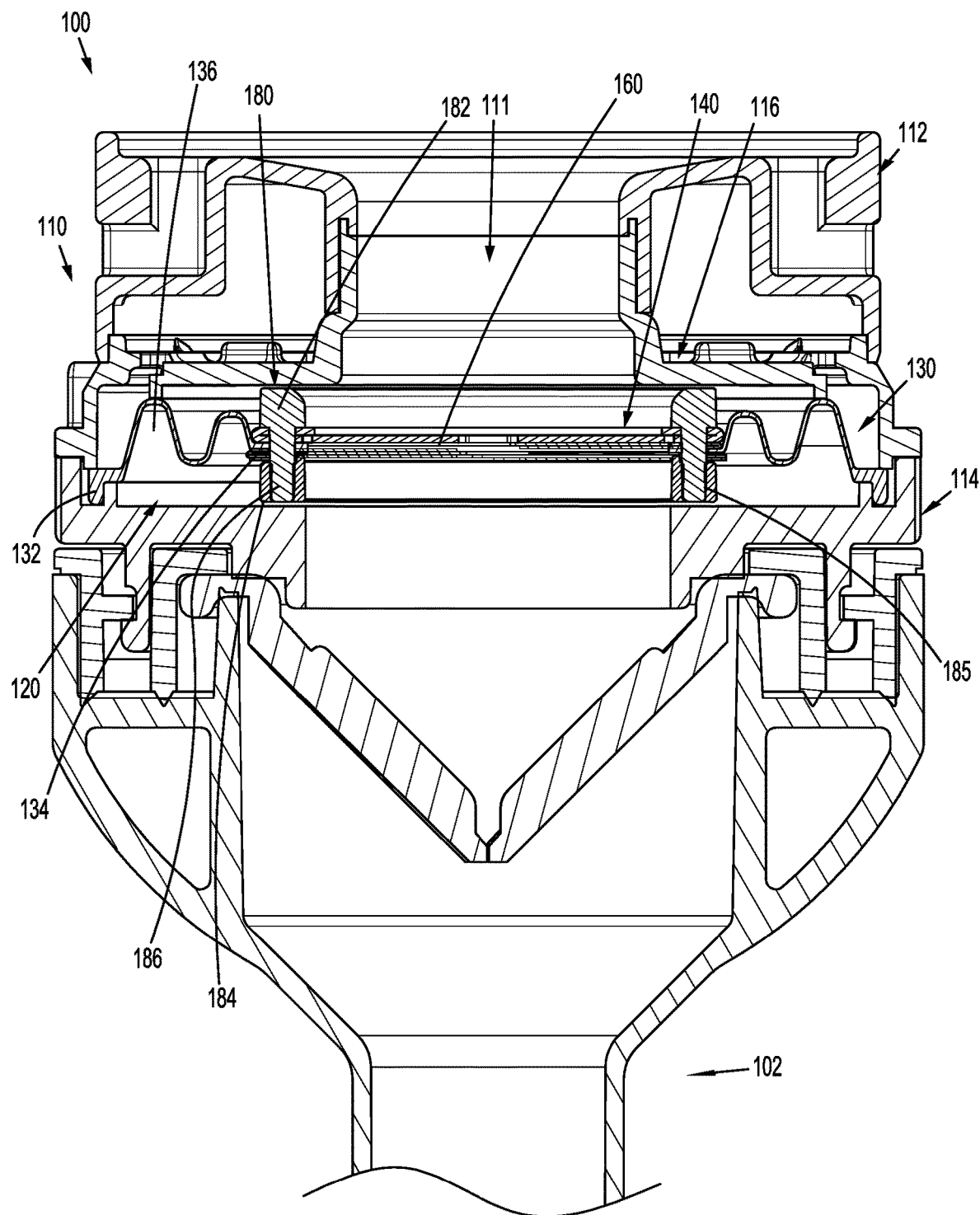
FIG. 2 a side cross-sectional view of the access assembly shown in FIG. 1 taken along section line 2-2.

With reference to FIG. 2, the instrument valve housing 110 of the access assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing section 112, 114 of the instrument valve housing 110 may be selectively attachable to, and detachable from, the inner housing section 116. The lower housing section 114 may be releasably or permanently attached to a cannula tube 104 (FIG. 1) of the access assembly 102. In embodiments, either or both of the upper and lower housing sections 112, 114 of the instrument valve housing 110 may include knurls, indentations, tabs, or be otherwise configured to facilitate engagement by a clinician.

The access assembly 100 may also include features for the stabilization of the access assembly. For example, the distal end of the cannula tube 104 may carry a balloon anchor or another expandable member that engages the abdomen from the interior side. For example, see commonly owned U.S. Pat. No. 7,300,448, the entire disclosure of which is hereby incorporated by reference herein. A feature on the opposite side of the abdominal wall may be used to further stabilize the access assembly, such as adhesive tabs or adjustable foam collars.

The upper, lower, and inner housing sections 112, 114, 116 of the instrument valve housing 110 define a longitudinal passage 111 for receipt of a surgical instrument (not shown). The valve assembly 120 is supported within the instrument valve housing 110 to provide sealed passage of the surgical instrument through the access assembly 100.

Figure 3:
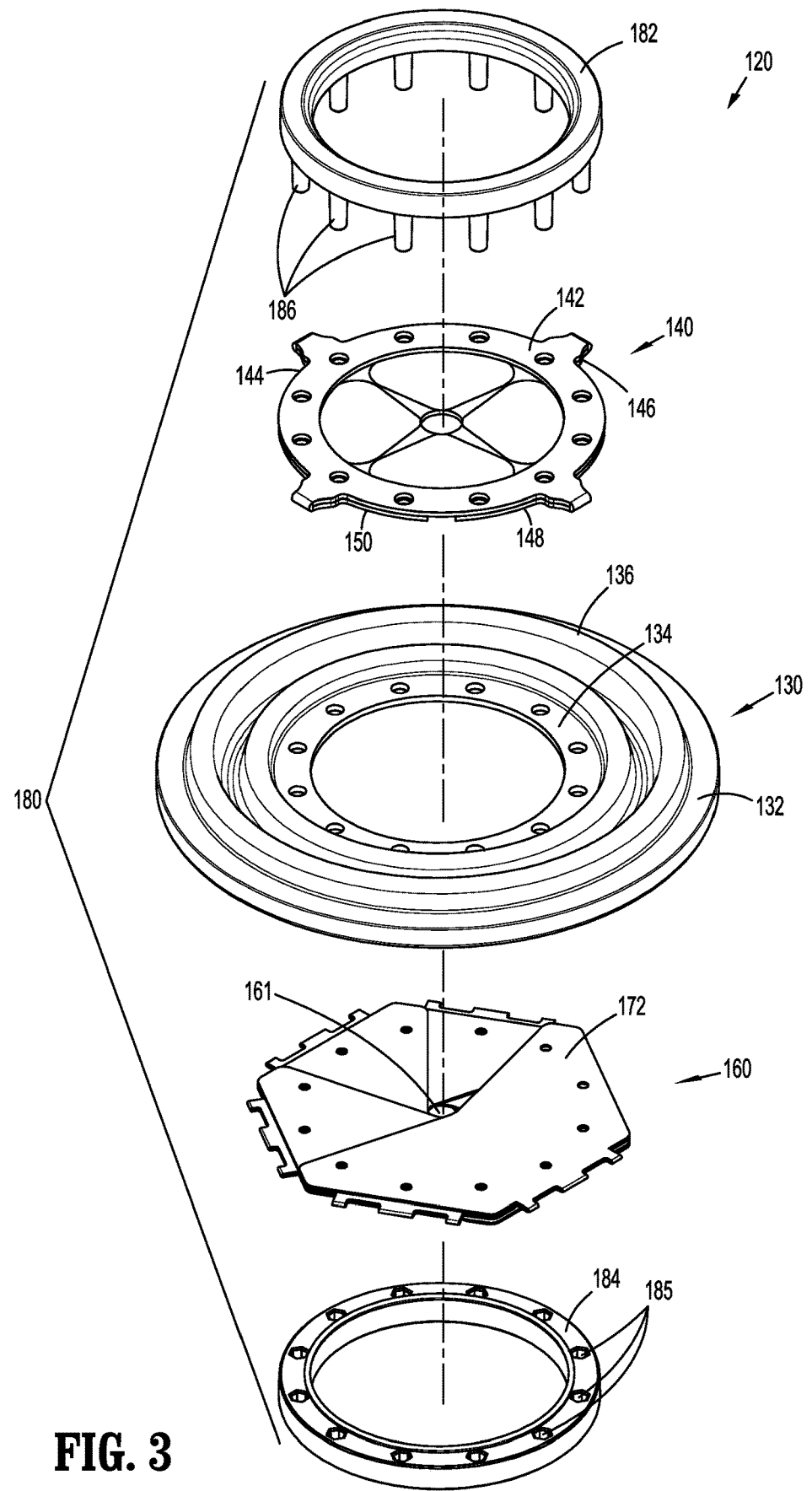
FIG. 3 is an exploded perspective view of a valve assembly, including a centering mechanism, a guard assembly, a seal assembly, and a retainer assembly.

With particular reference to FIGS. 2 and 3, the valve assembly 120 supported in the instrument valve housing 110 (FIG. 2) includes a centering mechanism 130, a guard assembly 140, a seal assembly 160, and a retainer assembly 180. The centering mechanism 130 of the valve assembly 120 permits radial movement of the valve assembly 120 relative to the instrument valve housing 110 when a surgical instrument is received through the valve assembly 120, and returns the valve assembly 120 to a generally centered position once the surgical instrument is withdrawn from within the instrument valve housing 110. The guard assembly 140 protects the seal assembly 160 during insertion and withdrawal of a surgical instrument through the seal assembly 160. The seal assembly 160 provides sealed passage of the surgical instrument through the instrument valve housing 110. The retainer assembly 180 maintains the centering mechanism 130, the guard assembly 140, and the seal assembly 160 in an aligned relationship with one another.

With continued reference to FIGS. 2 and 3, as noted above, the centering mechanism 130 of the valve assembly 120 is configured to maintain the valve assembly 120 centered within the instrument valve housing 110 (FIG. 2). In embodiments, and as shown, the centering mechanism 130 includes an outer annular ring 132, an inner annular ring 134, and a bellows 136 disposed between the outer annular ring 132 and the inner annular ring 134. As shown in FIG. 2, the outer annular ring 132 is received between the inner housing section 116 and the lower housing section 114 to retain the centering mechanism 130 within the instrument valve housing 110. The inner annular ring 134 supports the seal assembly 160. For a detailed description of the structure and function of an exemplary centering mechanism, please refer to commonly owned U.S. Pat. No. 6,702,787 ("the '787 patent"), the content of which is incorporated herein by reference in its entirety.

Although shown including the centering mechanism 130 having bellows 136, the valve assembly 120 may include alternative centering mechanisms. For example, the centering mechanism may include an annular base and a plurality of spokes extending from the base, as described in commonly owned U.S. Pat. App. Pub. No. 2015/0025477 ("the '477 publication"), the content of which is incorporated herein by reference in its entirety. It is envisioned that the centering mechanism may include multiple sets of spokes, as disclosed in the '477 publication.

Still referring to FIGS. 2 and 3, the guard assembly 140 of the valve assembly 120 includes a ring portion 142 and first, second, third, and fourth petals 144, 146, 148, 150. The guard assembly 140 may be formed from a sheet of plastic/polymeric material by stamping with a tool that forms the ring portion 142 and the petals 144, 146, 148, 150. Alternatively, the guard assembly 140 may be formed by molding or other techniques. It is envisioned that the guard assembly may include any number of petals, and the petals may include flap portions of any size or configuration. See, for example, U.S. Pat. Nos. 5,895,377 and 6,569,120 ("the '377 and '120 Patents"), and PCT Publication WO 91/12838, the entire disclosures of which are hereby incorporated by reference herein, for exemplary guard assemblies, as well as other aspects of access assemblies. For a detailed description of the structure and function of exemplary guard assemblies, please refer to commonly owned U.S. patent application Ser. Nos. 16/394,043, 16/238,823 and 62/916,931, the content of which is incorporated herein by reference in its entirety.

With particular reference now to FIGS. 4-11, the seal assembly 160 of the valve assembly 120 is configured to provide a seal around an outer surface of a surgical instrument (not shown) passing through the instrument valve housing 110 (FIG. 2).

Figure 4:
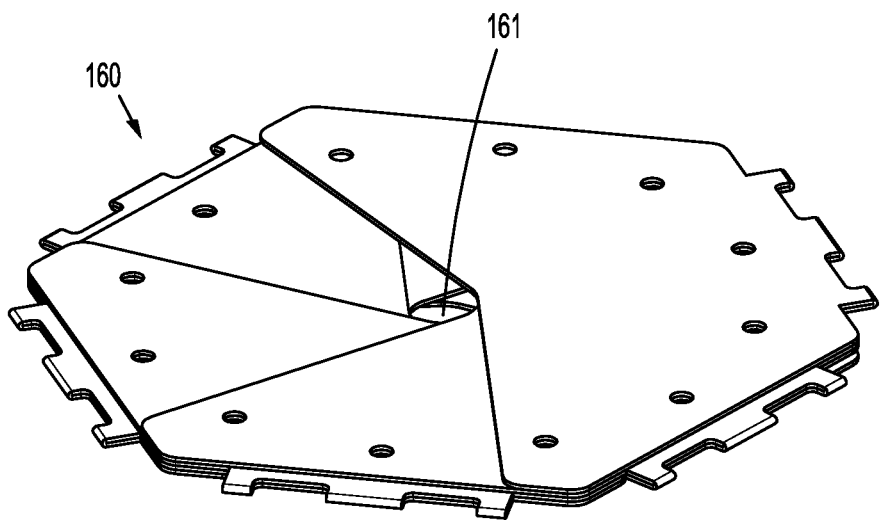
FIG. 4 is a perspective view of the seal assembly shown in FIG. 3.

The seal assembly 160 includes first, second, third, fourth, fifth, and sixth petals or sections 162, 164, 166, 168, 170, 172 movable from a first or unfolded configuration (FIG. 5) to folded configuration (FIG. 4). In the folded configuration, the seal assembly 160 forms a substantially planar, hexagonal member, with the first, second, third, fourth, fifth, and sixth sections 162, 164, 166, 168, 170, 172 of the seal assembly 160 defining an opening 161 therebetween to facilitate sealed passage of a surgical instrument (not shown) through the seal assembly 160. In embodiments, the opening 161 is 0.025" to 0.100" in diameter. By forming the opening 161 out of the first, second, third, fourth, fifth, and sixth sections 162, 164, 166, 168, 170, 172 of the seal assembly 160 instead of as a continuous solid opening through as single seal member, the likelihood of the seal assembly 160 tearing during insertion, removal, and use of a surgical instrument therethrough is greatly reduced. Although shown including six (6) sections, it is envisioned that the seal assembly 160 may include as few as four (4) sections, and as many as eight (8) sections.

The first, second, third, fourth, fifth, and sixth sections 162, 164, 166, 168, 170, 172 of the seal assembly 160 are formed of an elastic material, e.g., rubber, polyisoprenes, or silicone elastomers. In embodiments, the first, second, third, fourth, fifth, and sixth sections 162, 164, 166, 168, 170, 172 may include one or more fabric layers.

Figure 5:
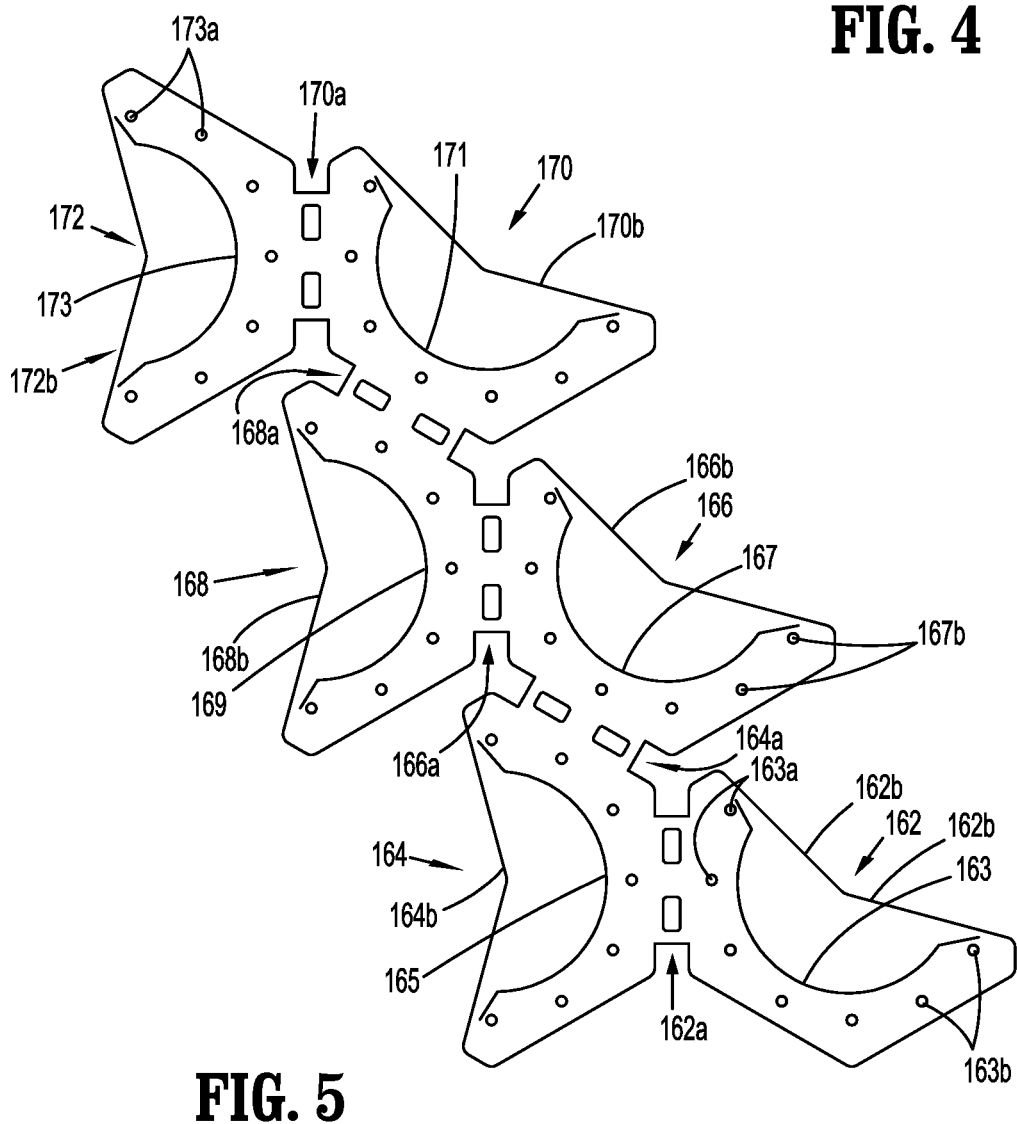
FIG. 5 is a perspective view of the seal assembly shown in FIG. 3, in an unfolded configuration.

With particular reference to FIG. 5, the first and second sections 162, 164 of the seal assembly 160, the second and third sections 164, 166, the third and fourth sections 166, 168, the fourth and fifth sections 168, 170, and the fifth and sixth section 170, 172 are connected to one another by a connector portion 162a, 164a, 166a, 168a, 170a, respectively. In embodiments, the connector portions 162a, 164a, 166a, 168a, 170a include a living hinge, or are otherwise formed to facilitate folding of the sections.

Figure 14:
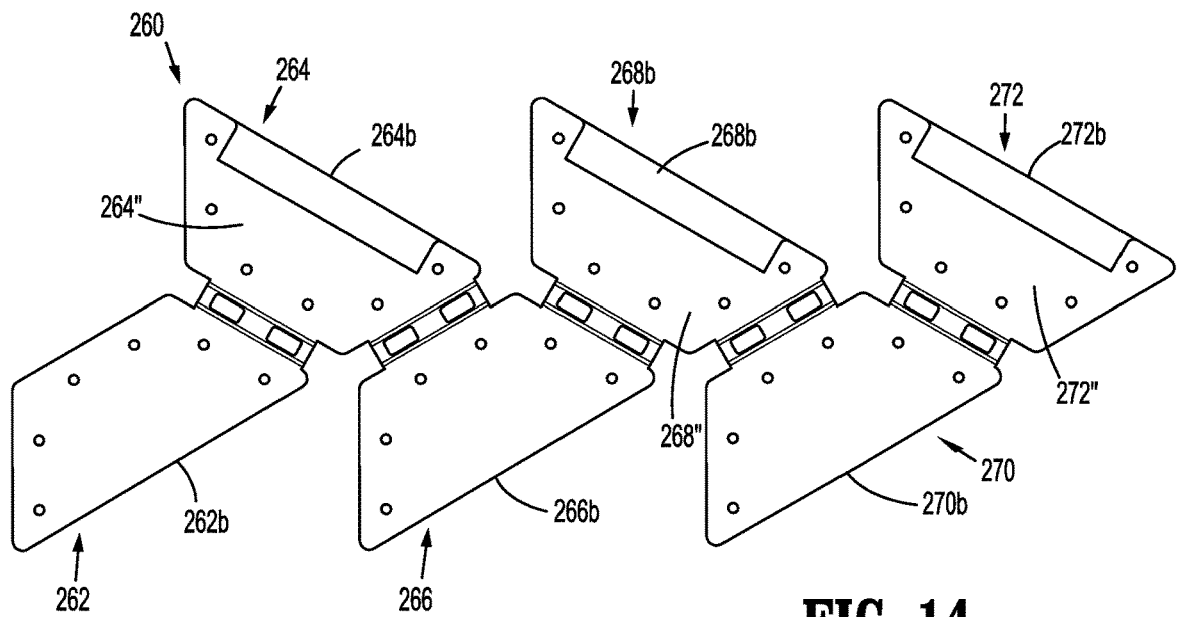
FIG. 14 is a top view of a seal assembly according to another embodiment of the present disclosure, in an initial or unfolded configuration.
Figure 15:
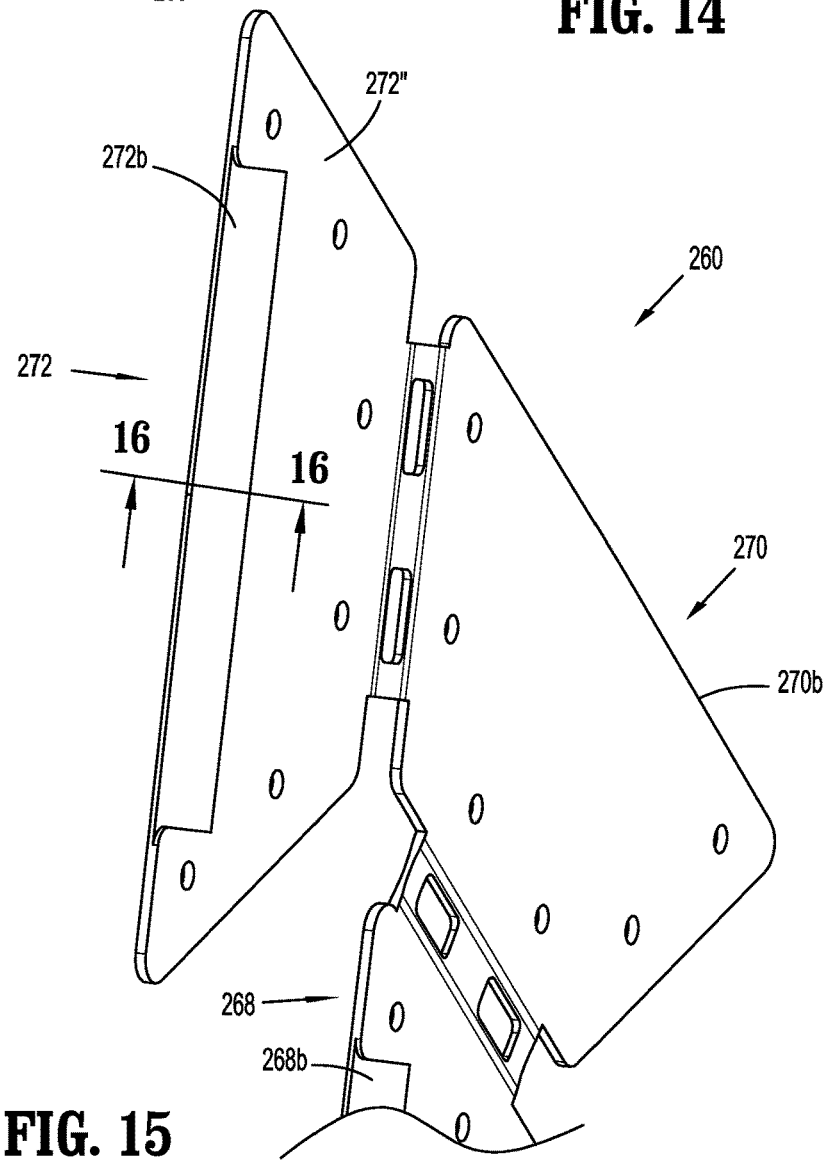
FIG. 15 is a perspective side view of a section of the seal assembly shown in FIG. 14.
Figure 16:
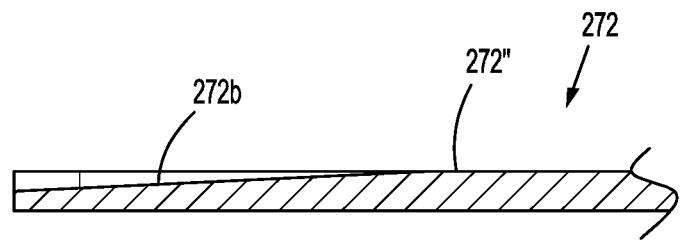
FIG. 16 is a side cross-sectional view of a section the seal assembly shown in FIG. 14 taken along section line 16-16 shown in FIG. 15.

An inner edge 162b, 164b, 166b, 168b, 170b, 172b of the respective first, second, third, fourth, fifth, and sixth sections 162, 164, 166, 168, 170, 172 of the seal assembly 160 may be straight (FIG. 14), or may define a V-shape (FIG. 5). In embodiments, the V-shape defines an angle between one-hundred eighty degrees (180°) and two-hundred seventy-five degrees (275°). The V-shape of the inner edges 162b, 164b, 166b, 168b, 170b facilitates reception of a surgical instrument (not shown) through the seal assembly 160.

Each of the first, second, third, fourth, fifth, and sixth sections 162, 164, 166, 168, 170, 172 of the seal assembly 160 includes a wing-shaped body that is configured to partially overlap the respective connected second, third, fourth, fifth, and sixth sections 164, 166, 168, 170, 172 when the seal assembly 160 is in the folded configuration. The first, second, third, fourth, fifth, and sixth sections 162, 164, 166, 168, 170, 172 are also configured to partially overlap the respective adjacent third, fourth, fifth, sixth, first, and second sections 166, 168, 170, 172, 162, 164 and the respective adjacent sixth, first, second, third, fourth, and fifth sections 172, 162, 164, 166, 168. For example, the first section 162 overlaps the connected second section 164, and the adjacent third and sixth sections 166, 172. In this manner, a portion of each of the first, second, third, fourth, fifth, and sixth sections 162, 164, 166, 168, 170, 172 overlaps three sections.

Each of the first, second, third, fourth, fifth, and sixth sections 162, 164, 166, 168, 170, 172 defines a plurality of openings 163, 165, 167, 169, 171, 173 along an outer perimeter of each section 162, 164, 166, 168, 170, 172. In embodiments, and as shown, the plurality of openings 163, 165, 167, 169, 171, 173 are arranged such the first and last two openings of each plurality of openings 163, 165, 167, 169, 171, 173 align with the last and first two openings of the adjacent sections. For example, as noted above, the first section 162 overlaps the connected second section 164 and the adjacent third and sixth sections 166, 177. In this manner, the first two openings 163a of the plurality of openings 163 align with last two openings 167b of the plurality of openings 167 in the third section 166, and the second two openings 163b of the plurality of openings 163 in the first section 162 align with the first two openings 173 of the plurality of openings 173 of the sixth section when the seal assembly 160 is in the folded configuration.

The plurality of openings 163, 165, 167, 169, 171, 173 are configured to receive pins 186 (FIG. 3) of the retainer assembly 180 to maintain the seal assembly 160 in the folded condition and to secure the seal assembly 160 relative to the guard assembly 140 and the centering mechanism 130.

Figure 6:
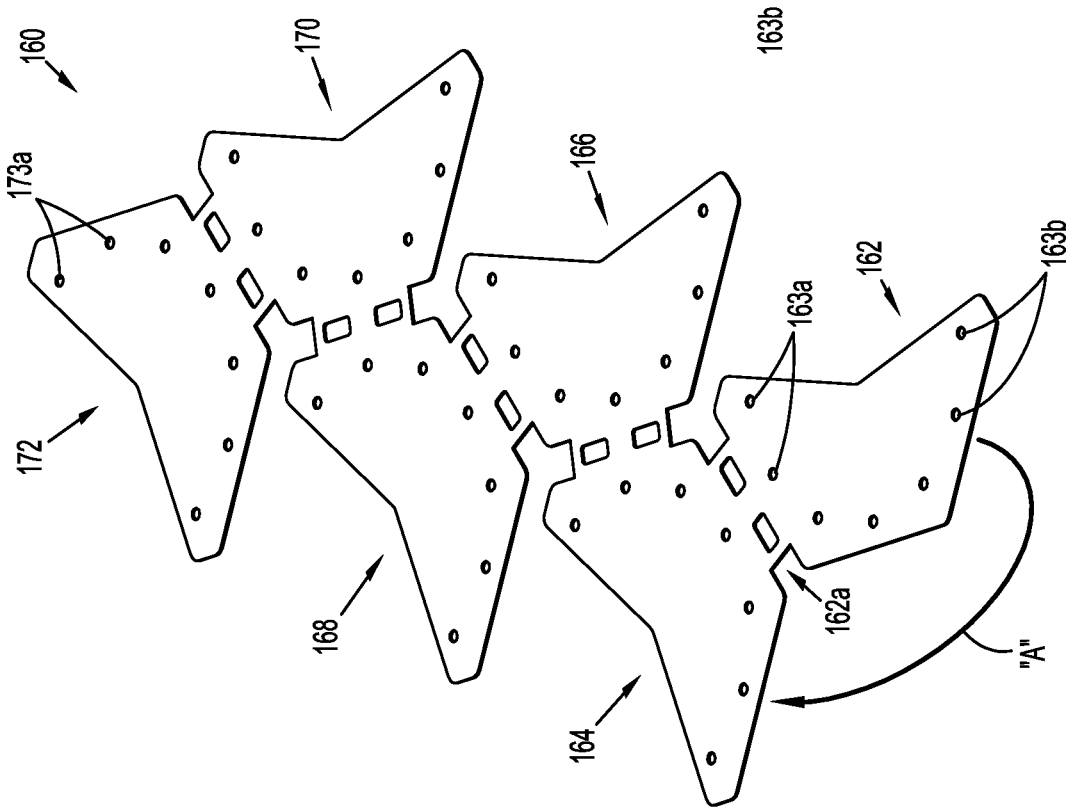

The method of folding the seal assembly 160 will now be described with reference to FIGS. 6-11. Referring initially to FIG. 6, the first section 162 of the seal assembly 160 is folded relative to the second section 164 at the hinge portion 162a between the first and second sections 162, 164, as indicated by arrow "A", such that a portion of the first section 162 adjacent the hinge portion 162a aligns with the portion of the second section 164 of the seal assembly 160 adjacent the hinge portion 162a. In this manner, the plurality of openings 163 in the portion of the first section 162 adjacent the hinge portion 162a aligns with the plurality of openings 165 in the overlapping portion of the second section 164 of the seal assembly 260 adjacent the hinge portions 162a.

Figure 7:
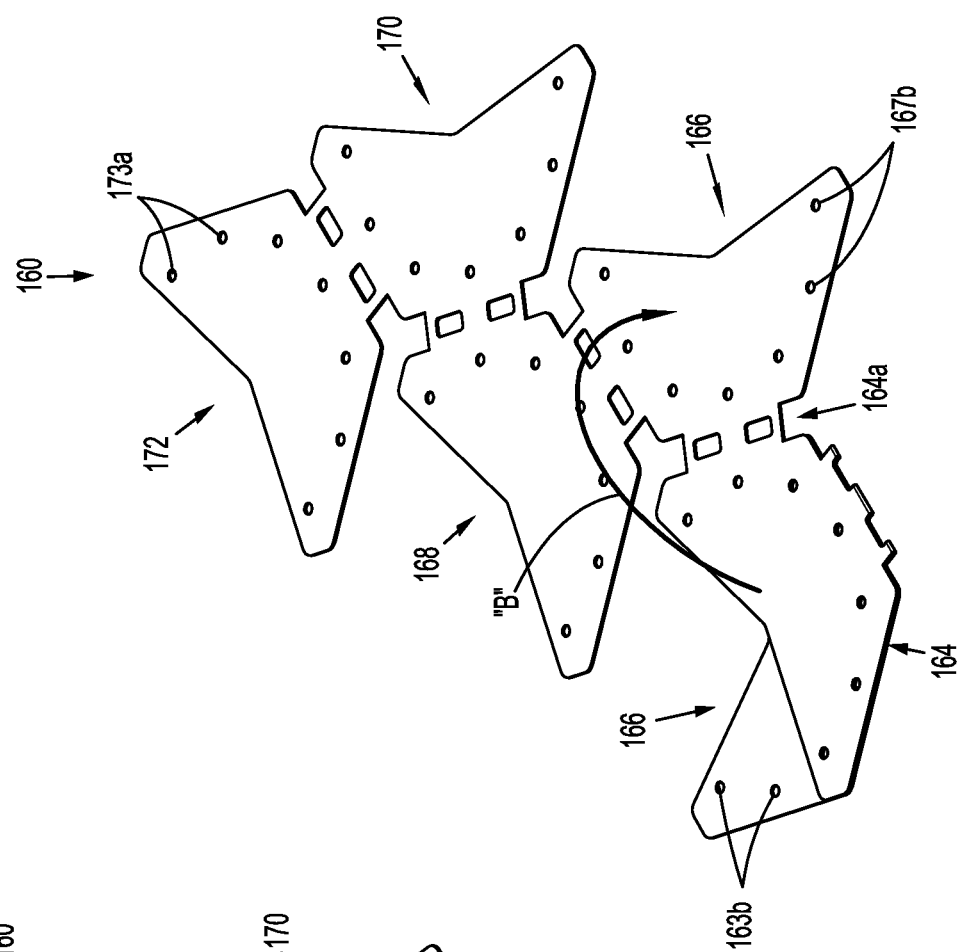
FIG. 6-11 are perspective views of the seal assembly shown in FIG. 3, in sequential partially folded conditions.

Turning to FIG. 7, the second section 164 of the seal assembly 160 is folded relative to the third section 166 at the hinge portion 164a between the second and third sections 164, 166, as indicated by arrow "B", such that a portion of the second section 164 adjacent the hinge portion 164a overlaps the length of the portion of the third section 166 of the seal assembly 160 adjacent the hinge portion 164a. In this manner, the plurality of openings 165 in the portion of the second section 164 adjacent the hinge portion 164a aligns with the plurality of openings 167 in the overlapping portion of the third section 166 of the seal assembly 160 adjacent the hinge portions 164a.

Figure 8:
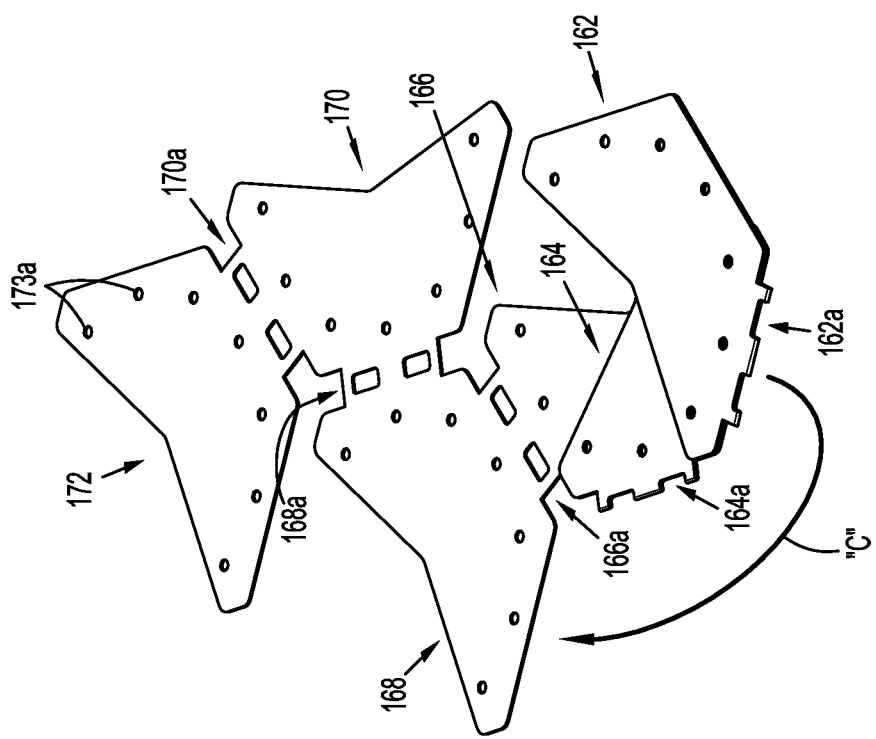

Referring to FIG. 8, the third section 166 of the seal assembly 160 is folded relative to the fourth section 168 of the seal assembly 160 at the hinge portion 166a between the third and fourth sections 166, 168, as indicated by arrow "C", such that the portion of the third section 166 adjacent the hinge portion 166a overlaps the portion of the fourth section 168 of the seal assembly 260 adjacent the hinge portion 166a. In this manner, the plurality of openings 167 in the portion of the third section 166 adjacent the hinge portion 166a aligns with the plurality of openings 169 in the overlapping portion of the fourth section 168 of the seal assembly 160 adjacent the hinge portions 166a.

Figure 9:
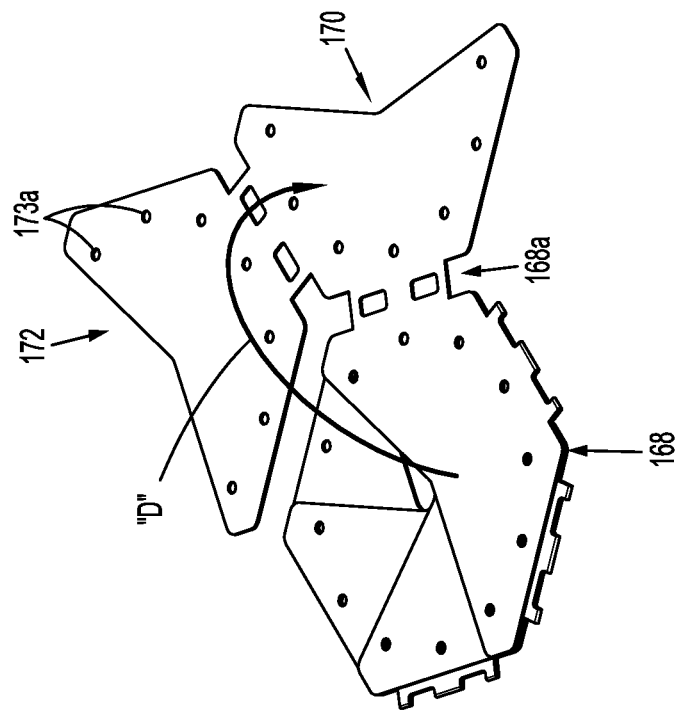

With reference to FIG. 9, the fourth section 168 of the seal assembly 160 is folded relative to the fifth section 170 of the seal assembly 160 at the hinge portion 168a between the fourth and fifth sections 168, 170, as indicated by arrow "D", such that the portion of the fourth section 168 adjacent the hinge portion 168a overlaps the portion of the fifth section 170 of the seal assembly 160 adjacent the hinge portion 168a. In this manner, the plurality of openings 169 in the portion of the fourth section 168 adjacent the hinge portion 168a aligns with the plurality of openings 171 in the overlapping portion of the fifth section 170 adjacent the hinge portion 168a.

Figure 10:
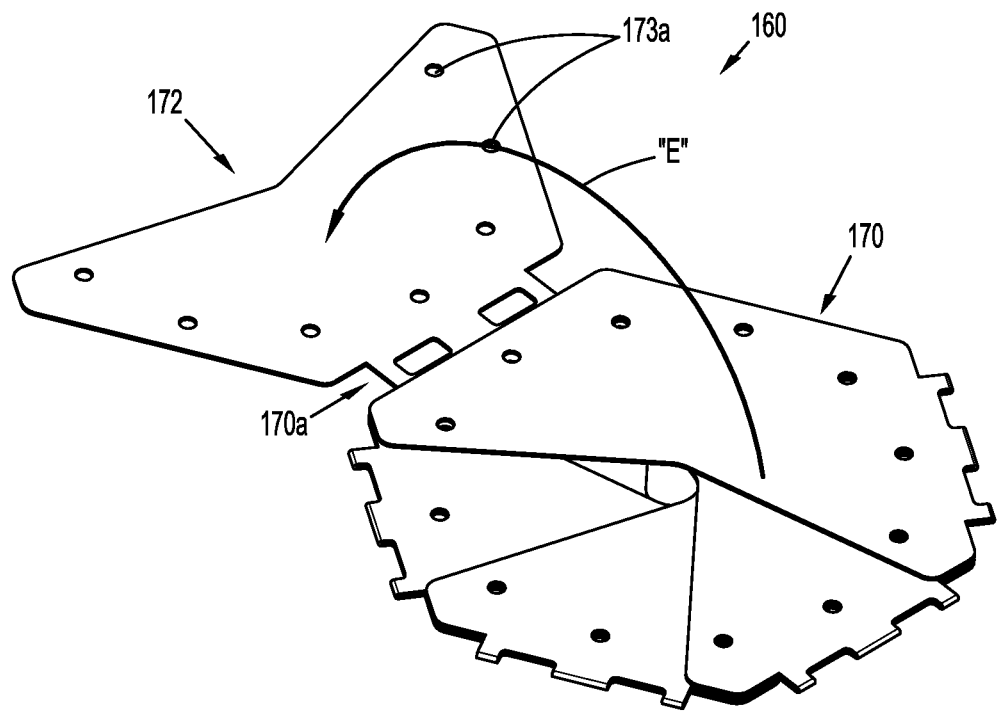
Figure 11:
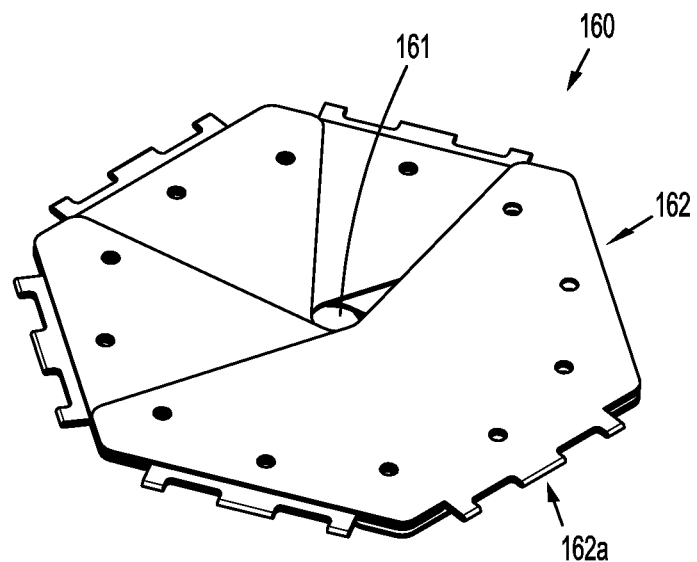
Figure 12:
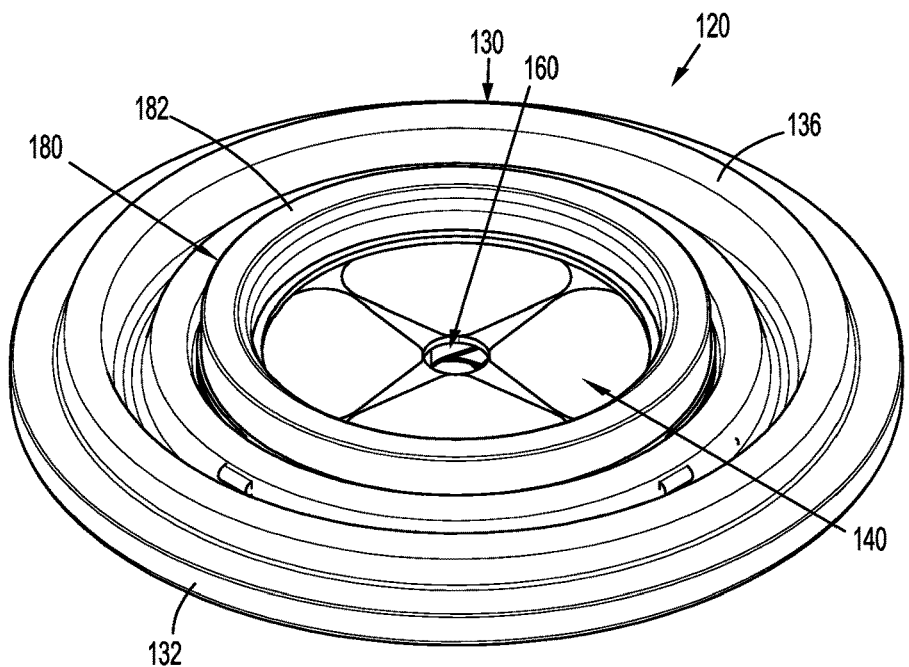
FIG. 12 is a top perspective view of the valve assembly shown in FIG. 3.
Figure 13:
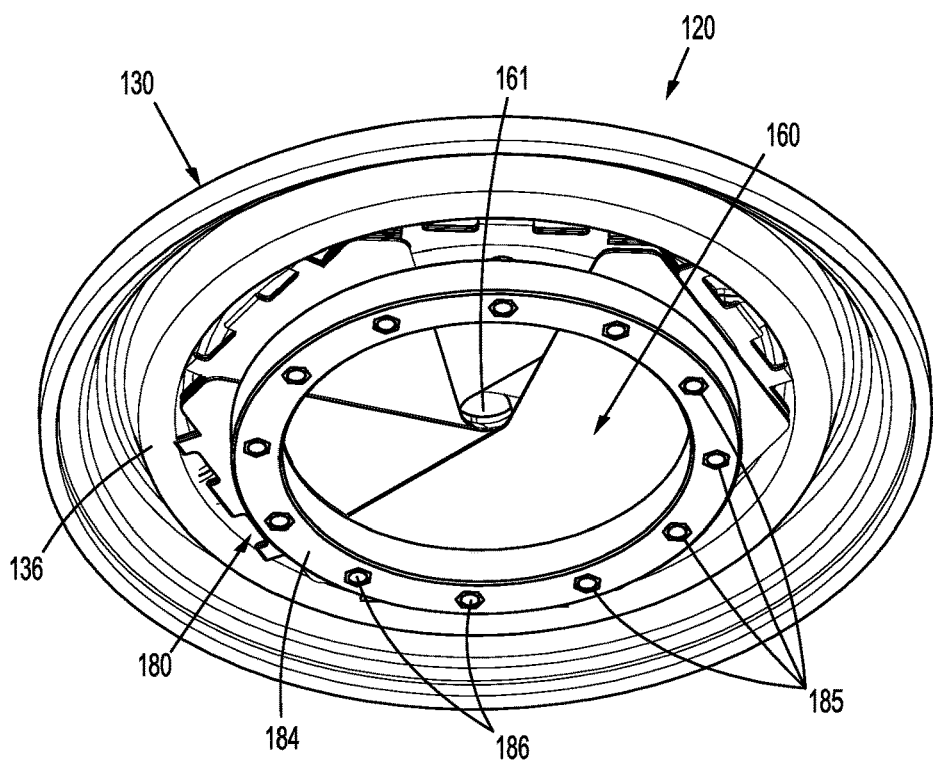
FIG. 13 is a bottom perspective view of the valve assembly shown in FIG. 3.

Turning to FIG. 10, the fifth section 170 of the seal assembly 160 is folded relative to the sixth section 172 at the hinge portion 170a between the fifth and sixth sections 170, 172, as indicated by arrow "E", such that the portion of the fifth section 170 adjacent the hinge portion 170a overlaps the portion of the sixth section 172 of the seal assembly 260 adjacent the hinge portion 170a. In this manner, the plurality of openings 171 in the portion of the fifth section 170 adjacent the hinge portion 170a aligns with the plurality of openings 173 in the overlapping portion of the sixth section 170 of the seal assembly 160 adjacent the hinge portion 170a.

In embodiments, a portion of the sixth section 172 of the seal assembly 160 is inserted under the first section 162 of the seal assembly 160 to interweave the first and sixth sections 162, 172. This interweaving increases the integrity of the seal assembly 160.

Referring back to FIGS. 2 and 3, the retainer assembly 180 of the valve assembly 120 is configured to secure the guard assembly 140 relative to the seal assembly 160, and secure the guard and seal assemblies 140, 160 to the centering mechanism 130. The retainer assembly 180 includes the upper retainer member 182, and a lower retainer member 184.

As noted above, the upper retainer member 182 includes a plurality of pins 186. The plurality of pins 186 extend from a bottom surface of the upper retainer member 182. Each pin of the plurality of pins 186 is configured to be lockingly received within an opening of a plurality of openings 185 (FIG. 3) of the lower retainer member 184. In embodiments, the plurality of pins 186 is welded, glued, adhered, bonded or otherwise secured within the plurality of openings 185 in the lower retainer member 184 to secure the upper retainer member 182 and the lower retainer member 184 together. Alternatively, the lower retainer member 184 may instead, or additionally, include a plurality of pins (not shown) with the upper retainer member 182 defining a plurality corresponding openings (not shown). Either or both of the upper and lower retainer members 182, 184 may include locking features (not shown) for engaging the plurality of pins and securing the upper retainer member 182 to the lower retainer member 184.

With particular reference to FIG. 2, the plurality of pins 186 of the upper retainer member 182 extend through the ring portion 142 of the guard assembly 140, through the seal assembly 160, through the inner annular ring 134 of the centering mechanism 130, and into the openings 185 in the lower retainer member 184.

During a surgical procedure utilizing access assembly 100, a surgical instrument (not shown) is introduced into the instrument valve housing 110 through the longitudinal passage 111 in the upper, lower, and inner housing sections 112, 114, 116. As described in the '377 and '120 Patents, the distal end of the surgical instrument engages the petals 144, 146, 148, 150 (FIG. 3) of the guard assembly 140 causing the respective petals 144, 146, 148, 150 to flex downward into contact with the seal assembly 160 to cause the central opening 163 of the seal assembly 162 to open to accommodate passage of the surgical instrument through the seal assembly. The guard assembly 130 minimizes damage to the seal assembly 160 during insertion of an instrument through the valve assembly 120. The guard assembly 130 operates to protect the seal 162 of the seal assembly 160 from tearing or other damage as a surgical instrument is received through and withdrawn from the seal assembly 160. As discussed above, the multi-petal configuration of the seal assembly 160 reduces the likelihood of the seal assembly 160 tearing during insertion and/or removal of the surgical instrument therethrough.

With reference now to FIGS. 14-17, a seal assembly according to another embodiment of the present disclosure is shown generally as seal assembly 260. The seal assembly 260 is substantially similar to the seal assembly 160 (FIGS. 4-11) described hereinabove, and will only be described in detail as relates to the differences therebetween.

Figure 17:
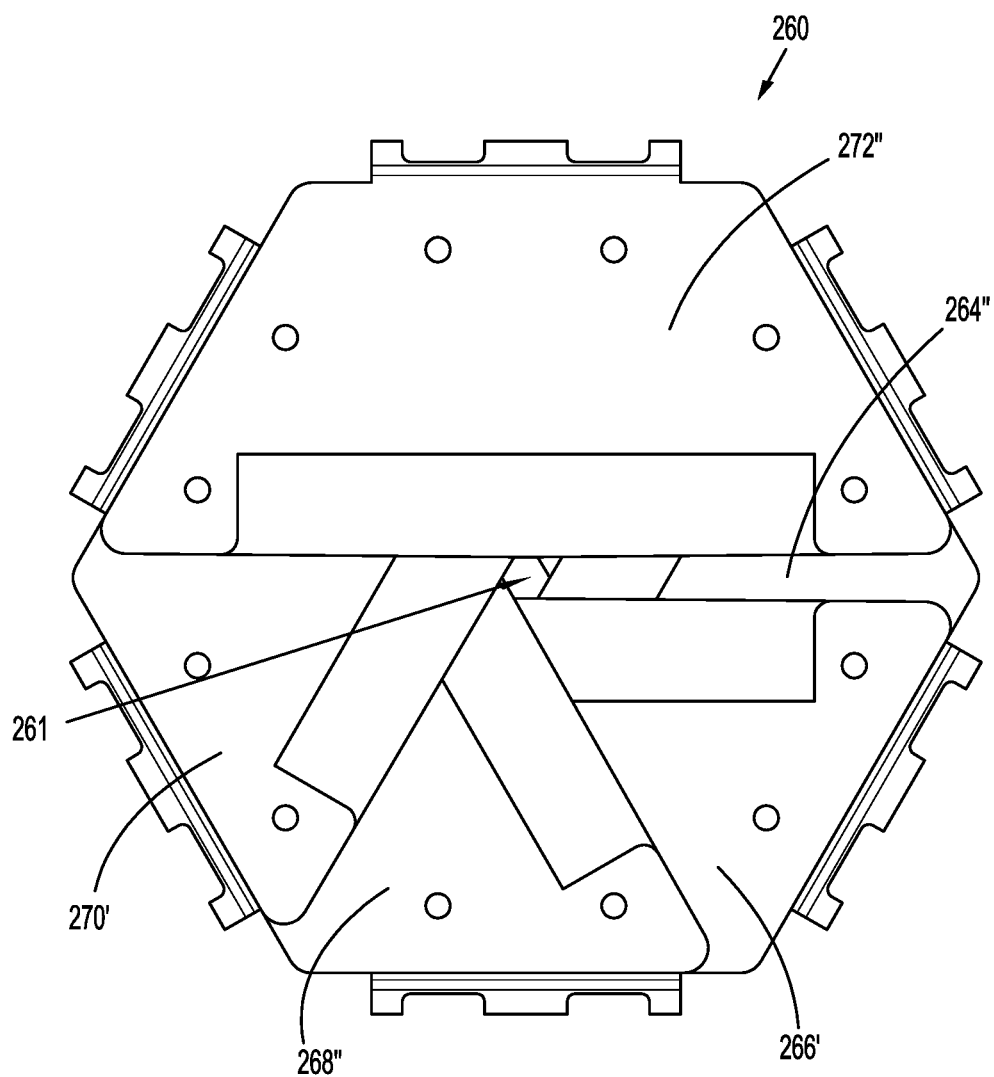
FIG. 17 is a top view of the seal assembly shown in FIG. 14, in a folded configuration.

The seal assembly 260 is configured to provide a seal around an outer surface of a surgical instrument (not shown) passing through the instrument valve housing 110 (FIG. 2). The seal assembly 260 includes first, second, third, fourth, fifth, and sixth petals or sections 262, 264, 266, 268, 270, 272 foldable from a first or unfolded configuration (FIG. 14) to folded configuration (FIG. 17). In the folded configuration the seal assembly 260 forms a substantially planar, hexagonal member, with the first, second, third, fourth, fifth, and sixth sections 262, 264, 266, 268, 270, 272 of the seal assembly 260 defining an opening 261 therebetween to facilitate sealed passage of a surgical instrument (not shown) through the seal assembly 260.

An inner edge 262b, 264b, 266b, 268b, 270b, 272b of the respective first, second, third, fourth, fifth, and sixth sections 262, 264, 266, 268, 270, 272 of the seal assembly 160 are tapered. The tapered inner edge 262b, 266b, 270b of the first, third, and fifth sections 262, 266, 270, respectively, is disposed on a first surface 262', 266', 270' (FIG. 17) of the respective first, third, and fifth sections 262, 266, 270 sections, and the tapered inner edge 264b, 268b, 272b of the second, fourth, and sixth sections 264, 268, 274, respectively, is disposed on a second surface 264", 268", 272" of the respective first, third, and fifth sections 262, 266, 270 sections. The tapered inner edge 262b, 264b, 266b, 268b, 270b, 272b of the respective first, second, third, fourth, fifth, and sixth sections 262, 264, 266, 268, 270, 272 facilitates sealed receipt of a surgical instrument through the opening 261 in the seal assembly 260.

The seal assembly 260 is secured within the instrument valve housing 110 (FIG. 2) in a similar manner to seal assembly 160 (FIGS. described hereinabove. The seal assembly 260 operates in a similar manner to seal assembly 160.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

The invention claimed is:

1. An access assembly comprising:
   an instrument valve housing including upper, lower, and inner housing sections and defining a cavity; and
   a valve assembly disposed within the cavity of the instrument valve housing, the valve assembly including:
      a guard assembly including a plurality of guard sections,
      a seal assembly disposed adjacent to the guard assembly, the seal assembly including a plurality of seal sections, the plurality of seal sections being movable from an unfolded configuration to a folded configuration in which the seal assembly forms a hexagonal member defining an opening to facilitate sealed passage of a surgical instrument; and
      a centering mechanism for maintaining the seal assembly and guard assembly centered within the cavity of the instrument valve.

2. The access assembly of claim 1, wherein the opening in the seal assembly has a diameter between 0.025" and 0.100".

3. The access assembly of claim 1, wherein the seal assembly includes six seal sections.

4. The access assembly of claim 1, wherein the plurality of seal sections are formed of polyisoprenes or silicone elastomers.

5. The access assembly of claim 1, wherein seal sections of the plurality of seal sections are connected to adjacent seal sections of the plurality of seal sections by connector portions.

6. The access assembly of claim 5, wherein the connector portion includes living hinges.

7. The access assembly of claim 1, wherein each seal section of the plurality of seal sections includes a wing shape.

8. The access assembly of claim 1, wherein an inner edge of each seal section of the plurality of seal sections is straight.

9. The access assembly of claim 1, wherein an inner edge of each seal section of the plurality of seal sections defines a V-shape.

10. The access assembly of claim 9, wherein the V-shape includes an angle between 180 degrees and 275 degrees.

11. The access assembly of claim 1, wherein an inner edge of each seal section of the plurality of seal sections is tapered.

12. The access assembly of claim 1, wherein the plurality of seal sections includes first, second, third, fourth, fifth, and sixth seal sections, each of the first, second, third, fourth, fifth, and sixth seal sections overlapping the adjacent second, third, fourth, fifth, sixth, and first seal sections.

13. The access assembly of claim 1, further including a retainer assembly including upper and lower retainer members.

14. The access assembly of claim 13, wherein at least one of the upper and lower retainer members includes a plurality of pins receivable through the guard assembly and seal assembly for retaining the guard and seal assemblies relative to each other.

15. The access assembly of claim 1, wherein the centering mechanism includes a bellows.

* * * * *

UNITED STATES PATENT AND TRADEMARK OFFICE
CERTIFICATE OF CORRECTION

| | | |
|---|---|---|
| PATENT NO. | : 10,792,071 B2 | Page 1 of 1 |
| APPLICATION NO. | : 16/272068 | |
| DATED | : October 6, 2020 | |
| INVENTOR(S) | : Pilletere et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this
Seventh Day of February, 2023

Katherine Kelly Vidal
*Director of the United States Patent and Trademark Office*